United States Patent [19]

Engelstad et al.

[11] Patent Number: 5,010,191

[45] Date of Patent: Apr. 23, 1991

[54] IMAGING AGENTS FOR IN VIVO MAGNETIC RESONANCE AND SCINTIGRAPHIC IMAGING

[75] Inventors: Barry L. Engelstad, Orinda; Kenneth N. Raymond, Berkeley; John P. Huberty, Corte Madera; David L. White, Oakland, all of Calif.

[73] Assignee: The Regents of the University of California, Oakland, Calif.

[21] Appl. No.: 767,214

[22] Filed: Aug. 19, 1985

[51] Int. Cl.$^5$ .......................................... C07D 241/08
[52] U.S. Cl. .................................... 544/225; 541/385
[58] Field of Search ........................ 544/385; 562/433; 436/173; 424/9; 128/653, 654

[56] References Cited

U.S. PATENT DOCUMENTS

| | | | |
|---|---|---|---|
| 3,901,890 | 8/1975 | Isowa et al. | 544/385 |
| 4,017,596 | 4/1977 | Loberg et al. | 556/107 |
| 4,313,926 | 2/1982 | Samochocka | 562/433 |
| 4,316,883 | 2/1982 | de Schrijver | 562/433 |
| 4,318,898 | 3/1982 | Molter et al. | 562/433 |
| 4,418,208 | 11/1983 | Nunn et al. | 562/450 |
| 4,472,509 | 9/1984 | Ganson et al. | 436/548 |
| 4,587,240 | 5/1986 | Hider et al. | 514/188 |
| 4,647,447 | 3/1987 | Gries et al. | 424/2 |
| 4,666,927 | 5/1987 | Hider et al. | 514/350 |
| 4,698,431 | 10/1987 | Raymond et al. | 546/298 |

FOREIGN PATENT DOCUMENTS

| | | | |
|---|---|---|---|
| 8633082 | 1/1983 | Australia . | |
| 0723317 | 2/1955 | United Kingdom | 562/565 |
| 0727465 | 4/1955 | United Kingdom | 562/565 |

OTHER PUBLICATIONS

Burt, W. R., Infection and Immunity, 990–996, vol. 35, No. 3 (Mar. 1982).
Collins, D. J., et al., Aust. J. Chemistry 27, 2593–2603 (1974).
Chemical Abstracts, vol. 82, No. 19, (1975): 124999v.
Chemical Abstracts, vol. 96, No. 23 (1982): 196226c.

*Primary Examiner*—Robert J. Warden
*Assistant Examiner*—Toni R. Scheiner
*Attorney, Agent, or Firm*—Flehr, Hohbach, Test, Albritton & Herbert

[57] ABSTRACT

Methods are provided for in vivo magnetic resonance imaging and/or scintigraphic imaging of a subject using chelated transition metal and lanthanide metal complexes. Novel ligands for these complexes are provided.

2 Claims, No Drawings

IMAGING AGENTS FOR IN VIVO MAGNETIC RESONANCE AND SCINTIGRAPHIC IMAGING

The Government has rights in this invention pursuant to Contract No. DE-AC03-76SF00098 awarded by the U.S. Department of Energy.

The present invention is directed to metal complexes useful as imaging agents for in vivo magnetic resonance imaging and scintigraphic imaging.

Magnetic resonance imaging of live subjects may be enhanced by the use of paramagnetic pharmaceuticals, such as paramagnetic metal chelates. Contrast agents for magnetic resonance imaging have heretofore been limited, among metal complexes, to metals chelated by nonspecific ligands such as DTPA (diethylenetriaminepentaacetic acid).

Another type of in vivo imaging which has found use in diagnostics is scintigraphic imaging whereby mildly radioactive isotopes are injected into the subject and an image is produced by scintigraphically imaging emission at selected photopeaks of acceptable energy (usually in the range of 70 to 400 keV). The radioactive isotopes should also be characterized by a sufficiently low absorbed radiation, which usually means a short physical half-life, and rapid biological clearance and/or low abundance of charged particulate emissions. Heretofore, clinical scintigraphic experience with paramagnetic elements has been quite limited. The use of isotopes of iron, manganese and chromium, trivalent cations exhibiting the largest magnetic moments, that is, the most potent paramagnetic effects, have generally been unsuitable for conventional scintigraphy. Moreover, among the paramagnetic agents which have been used for magnetic resonance imaging, or magnetic resonance spectroscopy, have not been effective for hepatobiliary contrast.

It is therefore an object of the present invention to provide metal complexes and paramagnetic metal complexes, which, in general, have use as scintigraphic imaging agents and/or magnetic resonance imaging agents.

It is a further object of the present invention to provide metal complexes which are useful for magnetic resonance imaging and/or magnetic resonance spectroscopy which are effective and safe for use as hepatobiliary contrast agents.

These and other objects will become apparent from the following description and claims.

SUMMARY OF THE INVENTION

The present invention is directed to novel metal complexes and the use thereof for magnetic resonance imaging and/or scintigraphic imaging for the in vivo study of tissues. The novel compounds include metal complexes wherein the ligand is of the following formulas I or II.

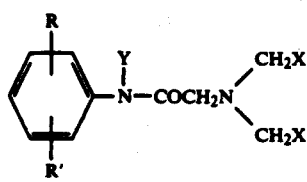
(I)

wherein $R$ and $R'$ are H, linear or branched alkyl of 1-6 carbon atoms; or $-OCH_2CH_2O_rCH_3$;

$X$ is $-CO_2-$, $-CON(R_2)O-$, $-NHCOR_3$, $-PO(OH)_2$, or $-COPO(OH)_2$;

$R_2$ is hydrogen or linear or branched alkyl of 1-6 carbon atoms;

$R_3$ is

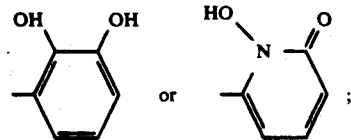

and $Y$ is H, linear or branched alkyl of 1-6 carbon atoms, or

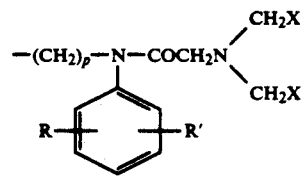

wherein p and r are integers greater than zero;

and

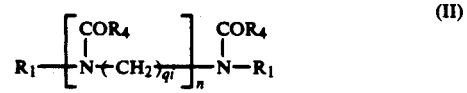
(II)

wherein $R_1$ is H or linear or branched alkyl of 1-6 carbon atoms;

$R_4$ is

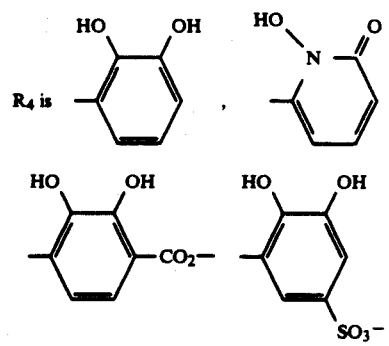

n is an integer greater than 1, each qi is an integer from 2 to 6; and i varies from 1 to n.

The present invention further provides methods of using metal complexes wherein the ligand is of formulas III, IV or V for magnetic resonance imaging and/or scintigraphic imaging:

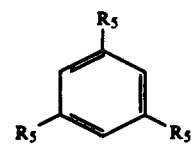
(III)

wherein $R_5$ is

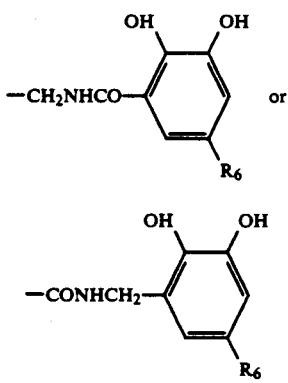

wherein $R_6$ is H or $-SO_3^-$;

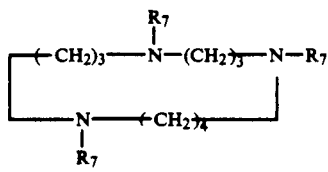

wherein $R_7$ is

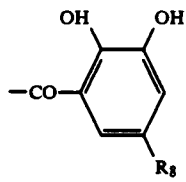

wherein $R_8$ is H or $-SO_3-$.

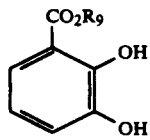

wherein $R_9$ is hydrogen or linear or branched alkyl of 1-6 carbon atoms.

DESCRIPTION OF THE INVENTION

One class of compounds according to the present invention are metal complexes wherein the ligand is of the following formula.

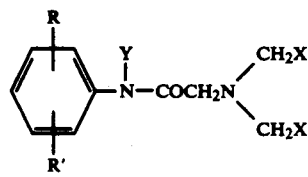

wherein
  R and R' are H, linear or branched alkyl of 1-6 carbon atoms; or $-OH_2CH_2O\text{,}CH_3$;
  X is $-CO_2-$, $-CON(R_2)O-$, $-NHCOR_3$, $-PO(OH)_2$, or $-COPO(OH)_2$;
  $R_2$ is hydrogen or linear or branched alkyl of 1-6 carbon atoms;
  $R_3$ is

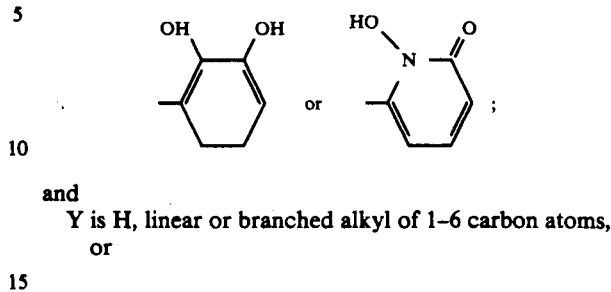

and
  Y is H, linear or branched alkyl of 1-6 carbon atoms, or

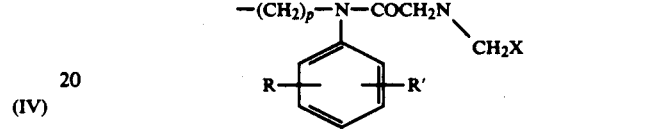

wherein
  p and r are integers greater than zero.

A preferred subclass of ligands of the formula I are those wherein Y is hydrogen. A particularly preferred class of ligands are those wherein Y is hydrogen and R and R' are both linear or branched alkyl of 1-6 carbon atoms.

The metal ion may be any metal ion which forms a complex with an above-described ligand and which, in its chelated form, is detectable by magnetic resonance or scintigraphic imaging.

A preferred ligand is that compound of formula I wherein Y is hydrogen, X is $CO_2-$ and R and R' are both ethyl at the 2 and 6 ring positions which is a particularly preferred ligand for the metal ion gadolinium-153.

The ligands according to the present invention having the formula I may be prepared by conventional techniques, such as by using an appropriate alpha-halo-R,R'- disubstituted acetanilide reactant with iminodiacetic acid. It will be understood that the above ligands of the formula I may form multiple ligands around a single metal ion. For example, in the complexes of lanthanide ions, there are usually 2-3 ligands of the formula I in the complex.

From the compounds of the formula I which are diacids (i.e., where an X is $CO_2H$ or its salt), desired diamides may be formed by conventional methods.

The corresponding phosphonic acid ($X=PO(OH)_2$), may be made by conventional methods. See, for example, Arbuzov, Pure Appl. Chem., 9:307-335 (1964).

The bridged ligands of the formula I, wherein Y is $(CH_2)_p-N-COCH_2N(CH_2X)_2$, may be generally prepared by any number of known routes. For example an appropriate aniline may be reacted with the bridging agent $Br(CH_2)_3Br$ to form the dianilino alkane. (Veer, Rec. Trav. Chim. 57, 33 (1935). The two amine groups may then be reacted with an appropriate acid. Alternatively, an appropriate Schiff base may be utilized formed by the reaction of a ketone with the diamino alkane. Reduction of the Schiff base by, for example, by hydrogenation over platinum oxide or Raney nickel, will yield the appropriately substituted diamino alkane. The two amino groups may be then treated with an appropriate acid to form the final diamide. See Wittbecker et al., JACS 69, 579 (1947); Ryabinin et al., *J. Appl. Chem. USSR*, 26, 369 (1953); and Klesbanski et al., *J. Gen. Chem. USSR*, 28, 1036 (1958).

The bridged compounds may also be formed by reacting an appropriate aniline with a dialdehyde to yield the Schiff base, the reduction of which by hydrogen over platinum oxide or Raney nickel result in the diamino alkane. The diamino alkane may then be treated with an appropriate acid or acid derivative to form the diamide.

The diamides may be converted to the final ligands by the usual routes. See Loberg et al., Nuclear Medicine Annual 1981, L. M. Freeman and H. S. Weissman, editors, Raven Press, New York 1981 (pp. 1–33). The diacetates which may be used to react with the diamino alkanes or acid anilides to form the ligand may be also formed by conventional methods. For example a secondary amine may be reacted with chloroacetyl chloride, followed by treatment with diaceto amine to form the diacetic acid (phenyl) $NYCOCH_2N(CH_2CO_2H)_2$. Alternatively, acetic anhydride may be treated with the diaceto amine, or a triaceto amine, to form cyclic imino anhydride. Treatment of the cyclic iminoanhydride with secondary amine will open the ring to form the (phenyl)$NYCOCH_2N(CH_2CO_2H)_2$.

The acetate groups on the final ligand may be replaced by other functional groups, such as, $PO(OH)_2$, $CON(R_2)OH$, $COPO(OH)_2$ and $NHCOR_3$, as shown in Formula I. A particularly preferred class of compounds of the formula I are those wherein R and R' are linear or branched alkyl of 1–6 carbon atoms. Particularly preferred are those compounds further wherein X is $CO_2^-$ and R and R' are on the 2 and 6 ring positions. The preferred metal ions chelated to such ligands include $Fe^{3+}$, $MN^{2+}$, $Gd^{3+}$, $Eu^{3+}$, $Cu^{2+}$, and $V^{2+}$, all of which are preferred relaxation probes for scintigraphy and magnetic imaging. Ions of iron, gadolinium, manganese, and chromium are particularly preferred for use in magnetic resonance. Also preferred are $Co^{2+}$, $Fe^{2+}$, and other trivalent lanthanides, which are useful shift probes for magnetic resonance imaging. For scintigraphy, suitably radioactive isotopes of these metals may be utilized, such as, isotopes of dysprosium, gadolinium, technetium, indium and gallium. The preferred radioactive ion is gadolinium-153. Other radioactive metal ions for scintigraphy include Gd-159, Gd-146, Gd-147, Dy-157, Dy-165, Dy-166, Eu-152, and Eu-157.

A second preferred class of ligands are those of the formula II. These are particularly useful for chelating iron ions. These may be prepared in general by known methods. See, for example, Weitl et al., J. Med. Chem., 24:203 (1981).

The ligands according to Formula II are particularly preferred for chelation of ferric ions, gadolinium (III) ions, manganese (II) ions and chromium (III) ions.

Two classes of particularly preferred ligands useful in the method according to the present invention are of the formulas VI and VII:

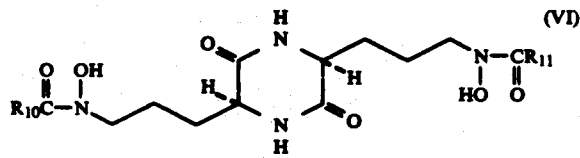

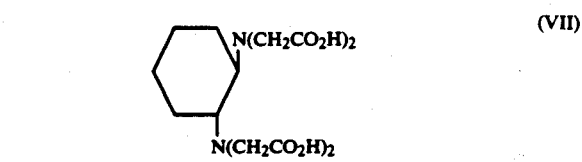

wherein $R_{10}$ and $R_{11}$ are independently alkyl of 1-6 carbon atoms, aryl of 5 to 20 carbon atoms, or $OR_{12}$, and $R_{12}$ is hydrogen, alkyl of 1-6 carbon atoms;

The preferred metal ions chelated to ligands of formula VI and VII are iron, gadolinium, manganese and chromium.

The complexes according to the present invention may be administered in any convenient manner to the subject in order to obtain localization of the ligand in the desired target tissues. The ligands may be dissolved in saline solution, or any convenient biologically acceptable carrier and injected, for example, intravenously. Other methods of administration may be utilized, such as, subcutaneous, parenteral methods, and the like. Selection of the formulation and method of administration is well within the skill of those of ordinary skill in the art.

In general, the dosages will be normally less than 1.0 mmole/kg body weight of the subject. A sufficient amount of the complex must be administered so that it will be detectable by magnetic resonance imaging or scintigraphy, depending on which method of detection is to be used. The usual dosage will be about 0.5 mmole/kg body weight of the subject.

Magnetic resonance imaging and magnetic resonance spectroscopy may be accomplished using conventionally available equipment for in vivo detection of substances by these techniques. The scintigraphic imaging may be accomplished using conventional and readily available equipment for in vivo studies. In the usual instance, isotopes having photopeaks in the range of about 70–400 keV will be suitable for detection by conventional scintigraphic equipment.

A particularly advantageous aspect of complex according to Formula I is that they are effective hepatobiliary contrast agents for magnetic resonance imaging and spectroscopy. Such complexes have urinary hepatobiliary pathways of excretion and therefore are particularly adapted for study of these tissues by magnetic resonance imaging. By utilizing the complex having a molecular weight greater than about 500 daltons, the urinary excretion pathway may be decreased, thereby enhancing the image in the hepatobiliary pathway.

The ligands of the formula I wherein R and R' are linear or branch alkyl 1-6 carbon atoms, and particularly wherein R and R' are at the 2 and 6 ring positions respectively, and wherein X is $CO_2$, are particularly useful as dual purpose imaging agents when used with suitable isotopes of metals. By dual purpose it is meant that their properties are suitable for both magnetic resonance imaging and scintigraphic imaging.

Ligands according to the formulas II, as well as III, IV and V are useful for the delineation of urinary or hepatobiliary structures. This is useful to improve the diagnosis of the urinary or hepatobiliary pathology, including tumors, gallstones and cholecystitis.

In general all of the complexes according to the present invention are generally useful to improve the imaging, by magnetic resonance and/or scintigraphy, of normal and abnormal tissues in the body, through specific and nonspecific mechanisms of localization. Furthermore, in general, the complexes according to the present invention shorten the imaging time required to produce and maintain the desired image of these target tissues.

Having described the preferred embodiments of the present invention, the following examples are presented for purpose of illustration, not by way of limitation.

EXAMPLE 1

Synthesis of bis-[(2,6-diethyl)-acetanilide-iminodiacetate]Gd(III) Complexes

1. Alpha-chloro 2,6 diethylacetanilide.
a. To 6.7 ml of chloroacetyl chloride in 100 ml dry acetone in an ice bath add slowly with nitrogen purge and stirring 22.06 ml of 2,6 diethyl aniline in 200 ml dry acetone.
b. Incubate for one hour at 4° C.
c. Bring to room temperature and stir for one hour.
d. Add 1200 ml USP water carefully to dissolve the aniline hydrochloride and precipitate the alpha-chloroacetanilide. Stir this mixture for 30 minutes.
e. Filter off the alpha-chloroacetanilide precipitate.
f. Suspend precipitate once in 1 liter 0.1 N HCl, refilter.
g. Suspend precipitate in 1 liter water USP, refilter.
h. Add 10 ml aqueous ethanol (1:1)/g of alpha-chloroacetanilide precipitate. Recrystallize ×3. Yield: approximately 50% of aniline converted to product.

2. N-2,6 diethylacetanilide-IDA.
a. 10 gm -chloro 2,6 diethylanilide is dissolved in 100 ml absolute ethanol.
b. 12 gm of iminodiacetic acid is dissolved in 90 ml of 2 N NaOH and diluted with 10 ml water.
c. These solutions are mixed, stirred and refluxed for 6 hours.
d. After refluxing evaporate solution to less than 100 ml.
e. Add water USP to 200 ml.
f. Wash solution ×3 with 100 ml diethyl ether.
g. Evaporate off residual ether.
h. Adjust pH to 2.0 with stirring and slow addition of 5 N HCL.
i. Store at 4° C. for 12 hours to precipitate the product.
j. To product add 500 ml of water USP and adjust pH to 7 with 10 N NaH to redissolve.
k. Reprecipitate at pH 2 with 5 N HCl. Repeat steps j and k.
l. Recrystallize product ×3 from 20 ml 85% ethanol/gm product. Yield: approximately 90%

3. Bis(2,6 diethyl-IDA) Gd
a. To 1 gm of 2,6 diethylacetanilide-IDA add 100 ml of anhydrous methanol (0.003 mole of 2,6 diethylanilideIDA).
b. Warm to solution.
c. Add 0.7 gm of Gd(NO .6H20 (0.0015 mole).
d. Warm solution and mix until Gd nitrate enters solution.
e. Add 4 drops of a methanol solution saturated with phenol red.
f. Titer to the yellow-red change using a methanol solution saturated with NaOH.
g. Reduce volume to 15 ml and adjust solution to a 4:7 ratio of acetone:methanol.
h. Baker Si25F TLC assay in 4:7, acetone:methanol gives a major peak at Rf 0.35 and a minor peak at Rf 0.79.
i. Process mixture containing excess ligand and sodium nitrate by flash chromatography using Baker Si250 silica gel. Elute column with 400 ml 4:7 acetone:methanol and fraction into 20 ml samples.
j. Maximum UV activity in samples 11-17. Combine these samples and remove solvent. Yield: approximately 80%.
k. Analyze hy HPLC, IR, elemental analysis, mass spectrometry.

This synthesis was carried out with naturally-occurring gadolinium (stable) and a radioisotope $^{153}$Gd.

EXAMPLE 2

The bis $^{153}$Gd complex of diethyl-acetanilide-iminodiacetate (prepared as in Example 1) and a control of $^{153}$GDCl$_3$ were administered to normal rats, and serial scintigrams wre obtained using a 20% window at approximately 100 keV. In separate tests, the corresponding complex using naturally-occurring (stable) gadolinium was administered to normal mice and rats, and tissue relaxation effects were assessed by magnetic resonance imaging and by measurements of tissue proton relaxation times in vitro. The results show that the scintigraphic mapping of a gadolinium isotope parallels the localization of a nonradioactive gadolinium analog and demonstrates the use of combined scintigraphic and magnetic resonance imaging with the same gadolinium compound.

EXAMPLE 3

Fe(III) complexes were subjected to a screening protocol that included: chemical characterization; determination of H T1 and T2 in vitro: assessment of the tolerance of an imaging dose in mice; bio-distribution and mass balance of $^{59}$Fe-labeled complex in mice; and sequential pre- and post-contrast (0.2 mmole/kg i.v.) dual spin echo (0.35 T; TR=0.5, 2.0 sec; TE=28, 56 msec) transaxial MRI of the upper abdomen in healthy rats. Magnetic resonance imaging enhancement was observed primarily in the kidneys. Some liver enhancement was noted with desferrioxame B. The results are shown in the Table below. The results appear to show that highly charged FE(III) complex are extracellular agents and exhibit largely renal clearance.

TABLE

FE (III) COMPLEX COMPARISON

| Ligand ("L") | Formula | Mol. Wt. | $1/T1^a$ | $1/T2^a$ | Toxicity$^b$ 0.5 | 1.0 |
|---|---|---|---|---|---|---|
| DTPA* | [FeL]$^{-2}$ | 444 | 0.68 | 0.89 | 2/2 | 2/2 |
| DF$^c$ | [FeL]$^{+1}$ | 615 | 1.7 | 1.9 | 2/2 | 2/2 |
| Tiron | [FeL3]$^{-9}$ | 854 | 2.6 | 3.0 | 2/2 | 0/2 |
| Di-iPr-3,4-LICAM-S$^d$ | [FeL]$^{-6}$ | 828 | 4.0 | 4.2 | 2/2 | 2/2 |
| 3,4,3-LICAM-C$^e$ | [FeL]$^{-7}$ | 969 | 1.4 | 1.9 | 0/2 | 0/2 |
| Oxine-sulfonate | [FeL$_3$]$^{-3}$ | 725 | 1.2 | 1.4 | 1/2 | 0/2 |
| (FeCl3) | [FeL(HOH$_6$)]$^{+3}$ | 164 | 3.6 | 4.8 | 0/2 | 0/2 |
| (Gd-DTPA) | [GdL]$^{-2}$ | 546 | 5.8 | 6.6 | 2/2 | 2/2 |

$^a$sec$^{-1}$ mmole$^{-1}$ at 10.7 MHz, 37° C., pH 7.5: 10.7 MHz.
$^b$mmole/kg i.p.; no. surviving at 24 hr/no. treated.
$^c$Desferrioxamine B.
$^d$2,3-Dimethyl-3,7,12-tris(2,3-dihydroxy-5-sulfobenzoyl)-3,7,12-triazatetradecane.
$^e$1,5,10,14-Tetrakis(2,3-dihydroxy-4-carboxybenzoyl)-1,5,10,14-tetraazatetradecane.
*Diethylenetriamine pentacetic acid.

We claim:
1. A metal complex comprising a metal ion complexed with a ligand of the Formula VI:

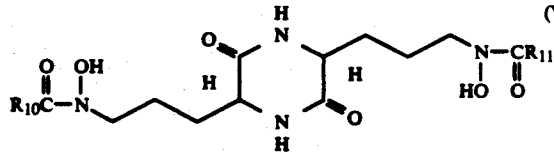 (VI)

wherein $R_{10}$ and $R_{11}$ are independently alkyl of 1-6 carbon atoms, aryl of 5 to 20 carbon atoms, or $OR_{12}$, wherein $R_{12}$ is hydrogen or alkyl of 1-6 carbon atoms.

2. A complex according to claim 1 wherein the metal ion of said complex is iron, gadolinium, manganese or chromium.

* * * * *

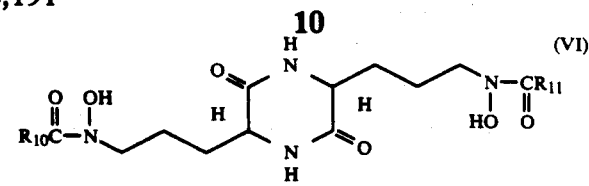 (VI)

wherein $R_{10}$ and $R_{11}$ are independently alkyl of 1-6 carbon atoms, aryl of 5 to 20 carbon atoms, or $OR_{12}$, wherein $R_{12}$ is hydrogen or alkyl of 1-6 carbon atoms.

2. A complex according to claim 1 wherein the metal ion of said complex is iron, gadolinium, manganese or chromium.

* * * * *

UNITED STATES PATENT AND TRADEMARK OFFICE
CERTIFICATE OF CORRECTION

PATENT NO. : 5,010,191

DATED : April 23, 1991

INVENTOR(S) : Barry L. Engelstad, et al

It is certified that error appears in the above-identified patent and that said Letters Patent is hereby corrected as shown below:

Column 2, line 2, -- "-O $CH_2CH_2O$ ,$CH_3$;" -- should read -- "-O$(CH_2CH_2O)_rCH_3$;"

Column 3, line 66, -- "O $H_2CH_2O$ ,$CH_3$;" -- should read -- "-O $(CH_2CH_2O)_rCH_3$;"

Column 7, line 56, -- "Gd(NO .6H2O" -- should read -- "Gd$(NO_3)_3$ · $6H_2O$"

Column 8, line 32, -- "in vitro: assessment" -- should read --in vitro; assessment--.

UNITED STATES PATENT AND TRADEMARK OFFICE
CERTIFICATE OF CORRECTION

PATENT NO.  : 5,010,191
DATED       : April 23, 1991
INVENTOR(S) : Barry L. Engelstad, et al It is certified that error appears in the above-identified patent and that said Letters Patent is hereby corrected as shown below:

Column 8, line 53, Table lines should read as follows:

| | | | | | | |
|---|---|---|---|---|---|---|
| Di-iPr-3,4-LICAM-S[d] | $[FeL]^{-6}$ | 828 | 4.0 | 4.2 | 2/2 | 2/2 |
| 3,4,3-LICAM[e] | $[FeL]^{-7}$ | 969 | 1.4 | 1.9 | 0/2 | 0/2 |
| Oxine-sulfonate | $[FeL]^{-3}$ | 725 | 1.2 | 1.4 | 1/2 | 0/2 |
| (FeCl3) | $[FeL(HOH_6)]^{+3}$ | 164 | 3.6 | 4.8 | 0/2 | 0/2 |
| (Gd-DTPA) | $[GdL]^{-2}$ | 546 | 5.8 | 6.6 | 2/2 | 2/2 |

Column 10, line 1-12 should be deleted

Signed and Sealed this

First Day of December, 1992

Attest:

DOUGLAS B. COMER

Attesting Officer    Acting Commissioner of Patents and Trademarks